(12) United States Patent
Yusupov

(10) Patent No.: US 11,337,888 B2
(45) Date of Patent: May 24, 2022

(54) POSTURE CORRECTION DEVICE

(71) Applicant: Fakhrikamal Yusupov, Mount Orab, OH (US)

(72) Inventor: Fakhrikamal Yusupov, Mount Orab, OH (US)

( * ) Notice: Subject to any disclaimer, the term of this patent is extended or adjusted under 35 U.S.C. 154(b) by 208 days.

(21) Appl. No.: 16/704,889

(22) Filed: Dec. 5, 2019

(65) Prior Publication Data

US 2020/0179221 A1 Jun. 11, 2020

Related U.S. Application Data

(60) Provisional application No. 62/775,411, filed on Dec. 5, 2018.

(51) Int. Cl.
*A61H 23/00* (2006.01)
*A61F 5/02* (2006.01)
*A61N 1/04* (2006.01)
*A61N 1/22* (2006.01)

(52) U.S. Cl.
CPC .............. *A61H 23/00* (2013.01); *A61F 5/026* (2013.01); *A61N 1/0408* (2013.01); *A61N 1/22* (2013.01); *A61H 2201/1607* (2013.01); *A61H 2201/1652* (2013.01); *A61H 2201/5005* (2013.01); *A61H 2205/08* (2013.01)

(58) Field of Classification Search
CPC ............ A61H 23/00; A61H 2201/1607; A61H 2201/1652; A61H 2201/5005; A61H 2205/08; A61F 5/026; A61N 1/0408; A61N 1/22
See application file for complete search history.

(56) References Cited

U.S. PATENT DOCUMENTS

| | | | |
|---|---|---|---|
| 7,207,953 B1* | 4/2007 | Goicaj | A61H 23/02 601/134 |
| 10,004,663 B2* | 6/2018 | Chao | A61N 1/36034 |
| 2005/0203586 A1* | 9/2005 | Yu | A61N 1/322 607/46 |
| 2015/0342826 A1* | 12/2015 | Chao | A61H 23/0263 601/70 |
| 2016/0151191 A1* | 6/2016 | Pond | A61H 23/02 602/19 |

* cited by examiner

*Primary Examiner* — Steven O Douglas
(74) *Attorney, Agent, or Firm* — Ariel S. Bentolila; Bay Area IP Group, LLC

(57) ABSTRACT

A posture correcting device using vibration or emitted electrical pulses in a pre-determined time sequence that may be adjusted in timing, intensity or strength, and a device for securing said posture correcting device to a body of a wearer.

20 Claims, 8 Drawing Sheets

POSTURE CORRECTION DEVICE

CROSS-REFERENCE TO RELATED APPLICATIONS

The present Utility patent application claims priority benefit of the [U.S. provisional application for patent Ser. No. 62/775,411 entitled "Deep Relaxed Belly Breathe Establisher, Posture Corrector, Concentration, Mindfulness, Meditative Techniques and Electro-magnetic massage", filed on Dec. 5, 2018 under 35 U.S.C. 119(e). The contents of this related provisional application are incorporated herein by reference for all purposes to the extent that such subject matter is not inconsistent herewith or limiting hereof.

RELATED CO-PENDING U.S. PATENT APPLICATIONS

Not applicable.

INCORPORATION BY REFERENCE OF SEQUENCE LISTING PROVIDED AS A TEXT FILE

Not applicable.

FEDERALLY SPONSORED RESEARCH OR DEVELOPMENT

Not applicable.

REFERENCE TO SEQUENCE LISTING, A TABLE, OR A COMPUTER LISTING APPENDIX

Not applicable.

COPYRIGHT NOTICE

A portion of the disclosure of this patent document contains material that is subject to copyright protection by the author thereof. The copyright owner has no objection to the facsimile reproduction by anyone of the patent document or patent disclosure for the purposes of referencing as patent prior art, as it appears in the Patent and Trademark Office, patent file or records, but otherwise reserves all copyright rights whatsoever.

BACKGROUND OF THE RELEVANT PRIOR ART

One or more embodiments of the invention generally relate to systems and methods for establishing deep, relaxed belly breathing, posture correction, concentration, mindfulness, meditative techniques and electro-magnetic massage. More particularly, certain embodiments of the invention relate to posture correction devices.

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon. Generally, people may develop shallow breathing patterns due to improper posture, exacerbating stress or discomfort in an individual, for which individuals may be unable to breathe diaphragmatically. Deep breathing may be beneficial in helping an individual remain calm in spite of potential stressors. Improper posture may lead to problems with the spine, central nervous system, gait, and the like, such as soreness, pain, or other discomfort. People may lack proper posture while both sitting and standing.

Healers from ancient times may have known that deep breathing is the key to a sound body. And, modern scientists of the world may have come to a conclusion for a long time that correct breathing is capable of prolonging life. And to do correct deep breathing more productive and vigorous. At deep breath, it may be important to involve the diaphragm. In other words it may be necessary to do a belly breathe. Bigger intake of oxygen in an organism may help burn more fat. Diaphragm (belly) breath may play the main role in expansion and strengthening of tissues of lungs. It may promote prevention of inflammation. Slow, deep breath may strengthen and make active parasympathetic system that promotes disposal of harmful salts. Such harmful salts may cause blood pressure jumps. Deep breath especially before going to bed, may calm the central nervous system and reduce psychological tension.

The following is an example of a specific aspect in the prior art that, while expected to be helpful to further educate the reader as to additional aspects of the prior art, is not to be construed as limiting the present invention, or any embodiments thereof, to anything stated or implied therein or inferred thereupon. By way of educational background, another aspect of the prior art generally useful to be aware of is that typically, meditation may be an option for some individuals in achieving diaphragmatic breathing, but people may be unaware how to develop proper meditation techniques on their own. Existing corsets may often be bulky and inefficient at correcting posture. These conventional corsets may lead to further discomfort in back muscles as well as restricting breathing, forcing people to abandon use. A woman's tightly fitting undergarment extending from below the chest to the hips, worn to shape the figure, may be inefficient at correcting posture. Accordingly, a posture correction device that is configured to conveniently remind a wearer to correct their posture and perform diaphragmatic breathing, is desired.

In view of the foregoing, it is clear that these traditional techniques are not perfect and leave room for more optimal approaches.

BRIEF DESCRIPTION OF THE DRAWINGS

The present invention is illustrated by way of example, and not by way of limitation, in the figures of the accompanying drawings and in which like reference numerals refer to similar elements and in which.

Figure 1:
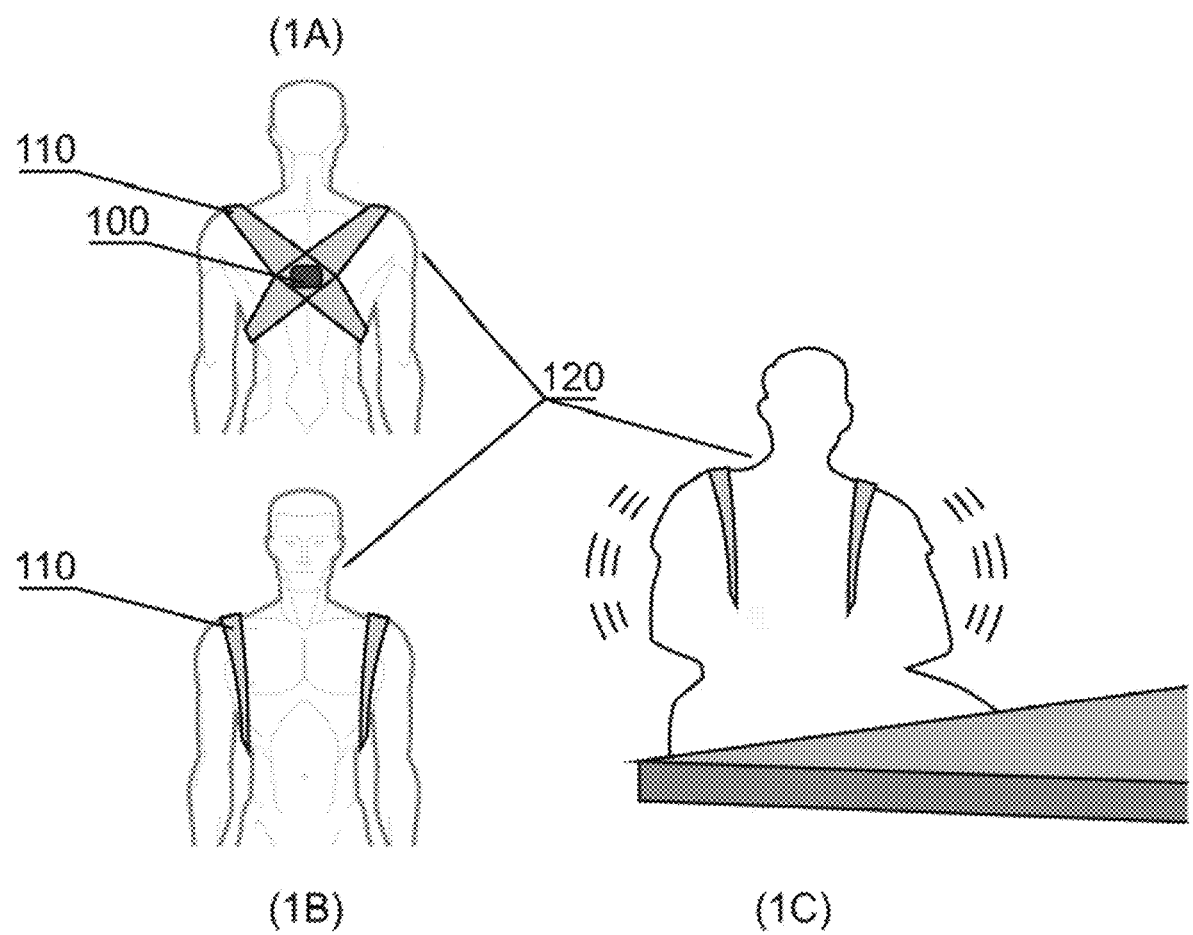
FIG. 1 shows a perspective view of an embodiment of the posture correction device while disposed on a wearer, in accordance with an embodiment of the present invention.

Unless otherwise indicated illustrations in the figures are not necessarily drawn to scale.

DETAILED DESCRIPTION OF SOME EMBODIMENTS

The term "rhomboidal" as used herein refers to, but not limited to, a parallelogram with unequal adjacent sides, especially one having oblique angles. For example, shaped like a rhombus or rhomboid.

The present invention is best understood by reference to the detailed figures and description set forth herein.

Embodiments of the invention are discussed below with reference to the Figures. However, those skilled in the art will readily appreciate that the detailed description given herein with respect to these figures is for explanatory purposes as the invention extends beyond these limited embodiments. For example, it should be appreciated that those skilled in the art will, in light of the teachings of the present invention, recognize a multiplicity of alternate and suitable approaches, depending upon the needs of the particular application, to implement the functionality of any given detail described herein, beyond the particular implementation choices in the following embodiments described and shown. That is, there are modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

It is to be further understood that the present invention is not limited to the particular methodology, compounds, materials, manufacturing techniques, uses, and applications, described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, for another example, a reference to "a step" or "a means" is a reference to one or more steps or means and may include sub-steps and subservient means. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

All words of approximation as used in the present disclosure and claims should be construed to mean "approximate," rather than "perfect," and may accordingly be employed as a meaningful modifier to any other word, specified parameter, quantity, quality, or concept. Words of approximation, include, yet are not limited to terms such as "substantial", "nearly", "almost", "about", "generally", "largely", "essentially", "closely approximate", etc.

As will be established in some detail below, it is well settled law, as early as 1939, that words of approximation are not indefinite in the claims even when such limits are not defined or specified in the specification.

For example, see Ex parte Mallory, 52 USPQ 297, 297 (Pat. Off. Bd. App. 1941) where the court said "The examiner has held that most of the claims are inaccurate because apparently the laminar film will not be entirely eliminated. The claims specify that the film is "substantially" eliminated and for the intended purpose, it is believed that the slight portion of the film which may remain is negligible. We are of the view, therefore, that the claims may be regarded as sufficiently accurate."

Note that claims need only "reasonably apprise those skilled in the art" as to their scope to satisfy the definiteness requirement. See Energy Absorption Sys., Inc. v. Roadway Safety Servs., Inc., Civ. App. 96-1264, slip op. at 10 (Fed. Cir. Jul. 3, 1997) (unpublished) Hybridtech v. Monoclonal Antibodies, Inc., 802 F.2d 1367, 1385, 231 USPQ 81, 94 (Fed. Cir. 1986), cert. denied, 480 U.S. 947 (1987). In addition, the use of modifiers in the claim, like "generally" and "substantial," does not by itself render the claims indefinite. See Seattle Box Co. v. Industrial Crating & Packing, Inc., 731 F.2d 818, 828-29, 221 USPQ 568, 575-76 (Fed. Cir. 1984).

Moreover, the ordinary and customary meaning of terms like "substantially" includes "reasonably close to: nearly, almost, about", connoting a term of approximation. See In re Frye, Appeal No. 2009-006013, 94 USPQ2d 1072, 1077, 2010 WL 889747 (B.P.A.I. 2010) Depending on its usage, the word "substantially" can denote either language of approximation or language of magnitude. Deering Precision Instruments, L.L.C. v. Vector Distribution Sys., Inc., 347 F.3d 1314, 1323 (Fed. Cir. 2003) (recognizing the "dual ordinary meaning of th[e] term ["substantially"] as connoting a term of approximation or a term of magnitude"). Here, when referring to the "substantially halfway" limitation, the Specification uses the word "approximately" as a substitute for the word "substantially" (Fact 4). (Fact 4). The ordinary meaning of "substantially halfway" is thus reasonably close to or nearly at the midpoint between the forwardmost point of the upper or outsole and the rearwardmost point of the upper or outsole.

Similarly, the term 'substantially' is well recognize in case law to have the dual ordinary meaning of connoting a term of approximation or a term of magnitude. See Dana Corp. v. American Axle & Manufacturing, Inc., Civ. App. 04-1116, 2004 U.S. App. LEXIS 18265, *13-14 (Fed. Cir. Aug. 27, 2004) (unpublished). The term "substantially" is commonly used by claim drafters to indicate approximation. See Cordis Corp. v. Medtronic AVE Inc., 339 F.3d 1352, 1360 (Fed. Cir. 2003) ("The patents do not set out any numerical standard by which to determine whether the thickness of the wall surface is 'substantially uniform.' The term 'substantially,' as used in this context, denotes approximation. Thus, the walls must be of largely or approximately uniform thickness."); see also Deering Precision Instruments, LLC v. Vector Distribution Sys., Inc., 347 F.3d 1314, 1322 (Fed. Cir. 2003); Epcon Gas Sys., Inc. v. Bauer Compressors, Inc., 279 F.3d 1022, 1031 (Fed. Cir. 2002). We find that the term "substantially" was used in just such a manner in the claims of the patents-in-suit: "substantially uniform wall thickness" denotes a wall thickness with approximate uniformity.

It should also be noted that such words of approximation as contemplated in the foregoing clearly limits the scope of claims such as saying 'generally parallel' such that the adverb 'generally' does not broaden the meaning of parallel. Accordingly, it is well settled that such words of approximation as contemplated in the foregoing (e.g., like the phrase 'generally parallel') envisions some amount of deviation from perfection (e.g., not exactly parallel), and that such words of approximation as contemplated in the foregoing are descriptive terms commonly used in patent claims to avoid a strict numerical boundary to the specified parameter. To the extent that the plain language of the claims relying on such words of approximation as contemplated in the foregoing are clear and uncontradicted by anything in the written description herein or the figures thereof, it is improper to rely upon the present written description, the figures, or the prosecution history to add limitations to any of the claim of the present invention with respect to such words of approximation as contemplated in the foregoing. That is, under such circumstances, relying on the written description and prosecution history to reject the ordinary and customary meanings of the words themselves is impermissible. See, for example, Liquid Dynamics Corp. v. Vaughan Co., 355 F.3d 1361, 69 USPQ2d 1595, 1600-01 (Fed. Cir. 2004). The plain language of phrase 2 requires a "substantial helical flow." The term "substantial" is a meaningful modifier implying "approximate," rather than "perfect." In Cordis Corp. v. Medtronic AVE, Inc., 339 F.3d 1352, 1361 (Fed. Cir. 2003), the district court imposed a precise numeric constraint on the term "substantially uniform thickness." We noted that the proper interpretation of this term was "of largely or approximately uniform thickness" unless something in the prosecution history imposed the "clear and unmistakable disclaimer" needed for narrowing beyond this simple-language interpretation. Id. In Anchor Wall Systems v. Rockwood Retaining Walls, Inc., 340 F.3d 1298, 1311 (Fed. Cir. 2003)" Id. at 1311. Similarly, the plain language of claim 1 requires neither a perfectly helical flow nor a flow that returns precisely to the center after one rotation (a limitation that arises only as a logical consequence of requiring a perfectly helical flow).

The reader should appreciate that case law generally recognizes a dual ordinary meaning of such words of approximation, as contemplated in the foregoing, as connoting a term of approximation or a term of magnitude; e.g., see Deering Precision Instruments, L.L.C. v. Vector Distrib. Sys., Inc., 347 F.3d 1314, 68 USPQ2d 1716, 1721 (Fed. Cir. 2003), cert. denied, 124 S. Ct. 1426 (2004) where the court was asked to construe the meaning of the term "substantially" in a patent claim. Also see Epcon, 279 F.3d at 1031 ("The phrase 'substantially constant' denotes language of approximation, while the phrase 'substantially below' signifies language of magnitude, i.e., not insubstantial."). Also, see, e.g., Epcon Gas Sys., Inc. v. Bauer Compressors, Inc., 279 F.3d 1022 (Fed. Cir. 2002) (construing the terms "substantially constant" and "substantially below"); Zodiac Pool Care, Inc. v. Hoffinger Indus., Inc., 206 F.3d 1408 (Fed. Cir. 2000) (construing the term "substantially inward"); York Prods., Inc. v. Cent. Tractor Farm & Family Ctr., 99 F.3d 1568 (Fed. Cir. 1996) (construing the term "substantially the entire height thereof"); Tex. Instruments Inc. v. Cypress Semiconductor Corp., 90 F.3d 1558 (Fed. Cir. 1996) (construing the term "substantially in the common plane"). In conducting their analysis, the court instructed to begin with the ordinary meaning of the claim terms to one of ordinary skill in the art. Prima Tek, 318 F.3d at 1148. Reference to dictionaries and our cases indicates that the term "substantially" has numerous ordinary meanings. As the district court stated, "substantially" can mean "significantly" or "considerably." The term "substantially" can also mean "largely" or "essentially." Webster's New 20th Century Dictionary 1817 (1983).

Words of approximation, as contemplated in the foregoing, may also be used in phrases establishing approximate ranges or limits, where the end points are inclusive and approximate, not perfect; e.g., see AK Steel Corp. v. Sollac, 344 F.3d 1234, 68 USPQ2d 1280, 1285 (Fed. Cir. 2003) where it where the court said [W]e conclude that the ordinary meaning of the phrase "up to about 10%" includes the "about 10%" endpoint. As pointed out by AK Steel, when an object of the preposition "up to" is nonnumeric, the most natural meaning is to exclude the object (e.g., painting the wall up to the door). On the other hand, as pointed out by Sollac, when the object is a numerical limit, the normal meaning is to include that upper numerical limit (e.g., counting up to ten, seating capacity for up to seven passengers). Because we have here a numerical limit—"about 10%"—the ordinary meaning is that that endpoint is included.

In the present specification and claims, a goal of employment of such words of approximation, as contemplated in the foregoing, is to avoid a strict numerical boundary to the modified specified parameter, as sanctioned by Pall Corp. v. Micron Separations, Inc., 66 F.3d 1211, 1217, 36 USPQ2d 1225, 1229 (Fed. Cir. 1995) where it states "It is well established that when the term "substantially" serves reasonably to describe the subject matter so that its scope would be understood by persons in the field of the invention, and to distinguish the claimed subject matter from the prior art, it is not indefinite." Likewise see Verve LLC v. Crane Cams Inc., 311 F.3d 1116, 65 USPQ2d 1051, 1054 (Fed. Cir. 2002). Expressions such as "substantially" are used in patent documents when warranted by the nature of the invention, in order to accommodate the minor variations that may be appropriate to secure the invention. Such usage may well satisfy the charge to "particularly point out and distinctly claim" the invention, 35 U.S.C. § 112, and indeed may be necessary in order to provide the inventor with the benefit of his invention. In Andrew Corp. v. Gabriel Elecs. Inc., 847 F.2d 819, 821-22, 6 USPQ2d 2010, 2013 (Fed. Cir. 1988) the court explained that usages such as "substantially equal" and "closely approximate" may serve to describe the invention with precision appropriate to the technology and without intruding on the prior art. The court again explained in Ecolab Inc. v. Envirochem, Inc., 264 F.3d 1358, 1367, 60 USPQ2d 1173, 1179 (Fed. Cir. 2001) that "like the term 'about,' the term 'substantially' is a descriptive term commonly used in patent claims to 'avoid a strict numerical boundary to the specified parameter, see Ecolab Inc. v. Envirochem Inc., 264 F.3d 1358, 60 USPQ2d 1173, 1179 (Fed. Cir. 2001) where the court found that the use of the term "substantially" to modify the term "uniform" does not render this phrase so unclear such that there is no means by which to ascertain the claim scope.

Similarly, other courts have noted that like the term "about," the term "substantially" is a descriptive term commonly used in patent claims to "avoid a strict numerical boundary to the specified parameter."; e.g., see Pall Corp. v.

Micron Seps., 66 F.3d 1211, 1217, 36 USPQ2d 1225, 1229 (Fed. Cir. 1995); see, e.g., Andrew Corp. v. Gabriel Elecs. Inc., 847 F.2d 819, 821-22, 6 USPQ2d 2010, 2013 (Fed. Cir. 1988) (noting that terms such as "approach each other," "close to," "substantially equal," and "closely approximate" are ubiquitously used in patent claims and that such usages, when serving reasonably to describe the claimed subject matter to those of skill in the field of the invention, and to distinguish the claimed subject matter from the prior art, have been accepted in patent examination and upheld by the courts). In this case, "substantially" avoids the strict 100% nonuniformity boundary.

Indeed, the foregoing sanctioning of such words of approximation, as contemplated in the foregoing, has been established as early as 1939, see Ex parte Mallory, 52 USPQ 297, 297 (Pat. Off. Bd. App. 1941) where, for example, the court said "the claims specify that the film is "substantially" eliminated and for the intended purpose, it is believed that the slight portion of the film which may remain is negligible. We are of the view, therefore, that the claims may be regarded as sufficiently accurate." Similarly, In re Hutchison, 104 F.2d 829, 42 USPQ 90, 93 (C.C.P.A. 1939) the court said "It is realized that "substantial distance" is a relative and somewhat indefinite term, or phrase, but terms and phrases of this character are not uncommon in patents in cases where, according to the art involved, the meaning can be determined with reasonable clearness."

Hence, for at least the forgoing reason, Applicants submit that it is improper for any examiner to hold as indefinite any claims of the present patent that employ any words of approximation.

Unless defined otherwise, all technical and scientific terms used herein have the same meanings as commonly understood by one of ordinary skill in the art to which this invention belongs. Preferred methods, techniques, devices, and materials are described, although any methods, techniques, devices, or materials similar or equivalent to those described herein may be used in the practice or testing of the present invention. Structures described herein are to be understood also to refer to functional equivalents of such structures. The present invention will be described in detail below with reference to embodiments thereof as illustrated in the accompanying drawings.

References to a "device," an "apparatus," a "system," etc., in the preamble of a claim should be construed broadly to mean "any structure meeting the claim terms" exempt for any specific structure(s)/type(s) that has/(have) been explicitly disavowed or excluded or admitted/implied as prior art in the present specification or incapable of enabling an object/aspect/goal of the invention. Furthermore, where the present specification discloses an object, aspect, function, goal, result, or advantage of the invention that a specific prior art structure and/or method step is similarly capable of performing yet in a very different way, the present invention disclosure is intended to and shall also implicitly include and cover additional corresponding alternative embodiments that are otherwise identical to that explicitly disclosed except that they exclude such prior art structure(s)/step(s), and shall accordingly be deemed as providing sufficient disclosure to support a corresponding negative limitation in a claim claiming such alternative embodiment(s), which exclude such very different prior art structure(s)/step(s) way(s).

From reading the present disclosure, other variations and modifications will be apparent to persons skilled in the art. Such variations and modifications may involve equivalent and other features which are already known in the art, and which may be used instead of or in addition to features already described herein.

Although Claims have been formulated in this Application to particular combinations of features, it should be understood that the scope of the disclosure of the present invention also includes any novel feature or any novel combination of features disclosed herein either explicitly or implicitly or any generalization thereof, whether or not it relates to the same invention as presently claimed in any Claim and whether or not it mitigates any or all of the same technical problems as does the present invention.

Features which are described in the context of separate embodiments may also be provided in combination in a single embodiment. Conversely, various features which are, for brevity, described in the context of a single embodiment, may also be provided separately or in any suitable subcombination. The Applicants hereby give notice that new Claims may be formulated to such features and/or combinations of such features during the prosecution of the present Application or of any further Application derived therefrom.

References to "one embodiment," "an embodiment," "example embodiment," "various embodiments," "some embodiments," "embodiments of the invention," etc., may indicate that the embodiment(s) of the invention so described may include a particular feature, structure, or characteristic, but not every possible embodiment of the invention necessarily includes the particular feature, structure, or characteristic. Further, repeated use of the phrase "in one embodiment," or "in an exemplary embodiment," "an embodiment," do not necessarily refer to the same embodiment, although they may. Moreover, any use of phrases like "embodiments" in connection with "the invention" are never meant to characterize that all embodiments of the invention must include the particular feature, structure, or characteristic, and should instead be understood to mean "at least some embodiments of the invention" include the stated particular feature, structure, or characteristic.

References to "user", or any similar term, as used herein, may mean a human or non-human user thereof. Moreover, "user", or any similar term, as used herein, unless expressly stipulated otherwise, is contemplated to mean users at any stage of the usage process, to include, without limitation, direct user(s), intermediate user(s), indirect user(s), and end user(s). The meaning of "user", or any similar term, as used herein, should not be otherwise inferred or induced by any pattern(s) of description, embodiments, examples, or referenced prior-art that may (or may not) be provided in the present patent.

References to "end user", "user", or any similar term, as used herein, is generally intended to mean late stage user(s) as opposed to early stage user(s). Hence, it is contemplated that there may be a multiplicity of different types of "end user" near the end stage of the usage process. Where applicable, especially with respect to distribution channels of embodiments of the invention comprising consumed retail products/services thereof (as opposed to sellers/vendors or Original Equipment Manufacturers), examples of an "end user" may include, without limitation, a "wearer", "consumer", "buyer", "customer", "purchaser", "shopper", "enjoyer", "viewer", or individual person or non-human thing benefiting in any way, directly or indirectly, from use of, or interaction, with some aspect of the present invention.

In some situations, some embodiments of the present invention may provide beneficial usage to more than one stage or type of usage in the foregoing usage process. In such cases where multiple embodiments targeting various stages of the usage process are described, references to "end user", or any similar term, as used therein, are generally intended to not include the user that is the furthest removed, in the foregoing usage process, from the final user therein of an embodiment of the present invention.

Where applicable, especially with respect to retail distribution channels of embodiments of the invention, intermediate user(s) may include, without limitation, any individual person or non-human thing benefiting in any way, directly or indirectly, from use of, or interaction with, some aspect of the present invention with respect to selling, vending, Original Equipment Manufacturing, marketing, merchandising, distributing, service providing, and the like thereof.

References to "person", "individual", "human", "a party", "animal", "creature", or any similar term, as used herein, even if the context or particular embodiment implies living user, maker, or participant, it should be understood that such characterizations are sole by way of example, and not limitation, in that it is contemplated that any such usage, making, or participation by a living entity in connection with making, using, and/or participating, in any way, with embodiments of the present invention may be substituted by such similar performed by a suitably configured non-living entity, to include, without limitation, automated machines, robots, humanoids, computational systems, information processing systems, artificially intelligent systems, and the like. It is further contemplated that those skilled in the art will readily recognize the practical situations where such living makers, users, and/or participants with embodiments of the present invention may be in whole, or in part, replaced with such non-living makers, users, and/or participants with embodiments of the present invention. Likewise, when those skilled in the art identify such practical situations where such living makers, users, and/or participants with embodiments of the present invention may be in whole, or in part, replaced with such non-living makers, it will be readily apparent in light of the teachings of the present invention how to adapt the described embodiments to be suitable for such non-living makers, users, and/or participants with embodiments of the present invention. Thus, the invention is thus to also cover all such modifications, equivalents, and alternatives falling within the spirit and scope of such adaptations and modifications, at least in part, for such non-living entities.

Headings provided herein are for convenience and are not to be taken as limiting the disclosure in any way.

The enumerated listing of items does not imply that any or all of the items are mutually exclusive, unless expressly specified otherwise.

It is understood that the use of specific component, device and/or parameter names are for example only and not meant to imply any limitations on the invention. The invention may thus be implemented with different nomenclature/terminology utilized to describe the mechanisms/units/structures/components/devices/parameters herein, without limitation. Each term utilized herein is to be given its broadest interpretation given the context in which that term is utilized.

Terminology. The following paragraphs provide definitions and/or context for terms found in this disclosure (including the appended claims):

"Comprising" And "contain" and variations of them— Such terms are open-ended and mean "including but not limited to". When employed in the appended claims, this term does not foreclose additional structure or steps. Consider a claim that recites: "A memory controller comprising a system cache . . . ." Such a claim does not foreclose the memory controller from including additional components (e.g., a memory channel unit, a switch).

"Configured To." Various units, circuits, or other components may be described or claimed as "configured to" perform a task or tasks. In such contexts, "configured to" or "operable for" is used to connote structure by indicating that the mechanisms/units/circuits/components include structure (e.g., circuitry and/or mechanisms) that performs the task or tasks during operation. As such, the mechanisms/unit/circuit/component can be said to be configured to (or be operable) for perform(ing) the task even when the specified mechanisms/unit/circuit/component is not currently operational (e.g., is not on). The mechanisms/units/circuits/components used with the "configured to" or "operable for" language include hardware—for example, mechanisms, structures, electronics, circuits, memory storing program instructions executable to implement the operation, etc. Reciting that a mechanism/unit/circuit/component is "configured to" or "operable for" perform(ing) one or more tasks is expressly intended not to invoke 35 U.S.C. sctn.112, sixth paragraph, for that mechanism/unit/circuit/component. "Configured to" may also include adapting a manufacturing process to fabricate devices or components that are adapted to implement or perform one or more tasks.

"Based On." As used herein, this term is used to describe one or more factors that affect a determination. This term does not foreclose additional factors that may affect a determination. That is, a determination may be solely based on those factors or based, at least in part, on those factors. Consider the phrase "determine A based on B." While B may be a factor that affects the determination of A, such a phrase does not foreclose the determination of A from also being based on C. In other instances, A may be determined based solely on B.

The terms "a", "an" and "the" mean "one or more", unless expressly specified otherwise.

All terms of exemplary language (e.g., including, without limitation, "such as", "like", "for example", "for instance", "similar to", etc.) are not exclusive of any other, potentially, unrelated, types of examples; thus, implicitly mean "by way of example, and not limitation . . . ", unless expressly specified otherwise.

Unless otherwise indicated, all numbers expressing conditions, concentrations, dimensions, and so forth used in the specification and claims are to be understood as being modified in all instances by the term "about." Accordingly, unless indicated to the contrary, the numerical parameters set forth in the following specification and attached claims are approximations that may vary depending at least upon a specific analytical technique.

The term "comprising," which is synonymous with "including," "containing," or "characterized by" is inclusive or open-ended and does not exclude additional, unrecited elements or method steps. "Comprising" is a term of art used in claim language which means that the named claim elements are essential, but other claim elements may be added and still form a construct within the scope of the claim.

As used herein, the phrase "consisting of" excludes any element, step, or ingredient not specified in the claim. When the phrase "consists of" (or variations thereof) appears in a clause of the body of a claim, rather than immediately following the preamble, it limits only the element set forth in that clause; other elements are not excluded from the claim as a whole. As used herein, the phrase "consisting essentially of" and "consisting of" limits the scope of a claim to the specified elements or method steps, plus those that do not materially affect the basis and novel characteristic(s) of the claimed subject matter (see Norian Corp. v Stryker Corp., 363 F.3d 1321, 1331-32, 70 USPQ2d 1508, Fed. Cir. 2004). Moreover, for any claim of the present invention which claims an embodiment "consisting essentially of" or "consisting of" a certain set of elements of any herein described embodiment it shall be understood as obvious by those skilled in the art that the present invention also covers all possible varying scope variants of any described embodiment(s) that are each exclusively (i.e., "consisting essentially of") functional subsets or functional combination thereof such that each of these plurality of exclusive varying scope variants each consists essentially of any functional subset(s) and/or functional combination(s) of any set of elements of any described embodiment(s) to the exclusion of any others not set forth therein. That is, it is contemplated that it will be obvious to those skilled how to create a multiplicity of alternate embodiments of the present invention that simply consisting essentially of a certain functional combination of elements of any described embodiment(s) to the exclusion of any others not set forth therein, and the invention thus covers all such exclusive embodiments as if they were each described herein.

With respect to the terms "comprising," "consisting of," and "consisting essentially of," where one of these three terms is used herein, the disclosed and claimed subject matter may include the use of either of the other two terms. Thus in some embodiments not otherwise explicitly recited, any instance of "comprising" may be replaced by "consisting of" or, alternatively, by "consisting essentially of", and thus, for the purposes of claim support and construction for "consisting of" format claims, such replacements operate to create yet other alternative embodiments "consisting essentially of" only the elements recited in the original "comprising" embodiment to the exclusion of all other elements.

Moreover, any claim limitation phrased in functional limitation terms covered by 35 USC § 112(6) (post AIA 112(f)) which has a preamble invoking the closed terms "consisting of," or "consisting essentially of," should be understood to mean that the corresponding structure(s) disclosed herein define the exact metes and bounds of what the so claimed invention embodiment(s) consists of, or consisting essentially of, to the exclusion of any other elements which do not materially affect the intended purpose of the so claimed embodiment(s).

Devices or system modules that are in at least general communication with each other need not be in continuous communication with each other, unless expressly specified otherwise. In addition, devices or system modules that are in at least general communication with each other may communicate directly or indirectly through one or more intermediaries. Moreover, it is understood that any system components described or named in any embodiment or claimed herein may be grouped or sub-grouped (and accordingly implicitly renamed) in any combination or sub-combination as those skilled in the art can imagine as suitable for the particular application, and still be within the scope and spirit of the claimed embodiments of the present invention. For an example of what this means, if the invention was a controller of a motor and a valve and the embodiments and claims articulated those components as being separately grouped and connected, applying the foregoing would mean that such an invention and claims would also implicitly cover the valve being grouped inside the motor and the controller being a remote controller with no direct physical connection to the motor or internalized valve, as such the claimed invention is contemplated to cover all ways of grouping and/or adding of intermediate components or systems that still substantially achieve the intended result of the invention.

A description of an embodiment with several components in communication with each other does not imply that all such components are required. On the contrary a variety of optional components is described to illustrate the wide variety of possible embodiments of the present invention.

As is well known to those skilled in the art many careful considerations and compromises typically must be made when designing for the optimal manufacture of a commercial implementation any system, and in particular, the embodiments of the present invention. A commercial implementation in accordance with the spirit and teachings of the present invention may configured according to the needs of the particular application, whereby any aspect(s), feature(s), function(s), result(s), component(s), approach(es), or step(s) of the teachings related to any described embodiment of the present invention may be suitably omitted, included, adapted, mixed and matched, or improved and/or optimized by those skilled in the art, using their average skills and known techniques, to achieve the desired implementation that addresses the needs of the particular application.

In the following description and claims, the terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

It is to be understood that any exact measurements/dimensions or particular construction materials indicated herein are solely provided as examples of suitable configurations and are not intended to be limiting in any way. Depending on the needs of the particular application, those skilled in the art will readily recognize, in light of the following teachings, a multiplicity of suitable alternative implementation details.

Some embodiments of the present invention and variations thereof, relate to systems and methods for establishing deep, relaxed belly breathing, posture correction, concentration, mindfulness, meditative techniques and electromagnetic massage. In one embodiment of the present invention, the posture correction device may include a housing having an adjustable strap that secures the housing to either the torso or waist of a wearer. The housing may include an adhesive tab that secures the housing to the wearer. The base may include an internal vibration mechanism adapted to vibrate or emit weak electrical pulses in a pre-determined time sequence in order to promote the health and well-being of the wearer. The device may further include controls to adjust the timing and intensity of the electrical pulses or vibrations. In other embodiments, the device may include a wireless transceiver that may enable the internal vibration mechanism to be wirelessly controlled via a smartphone or other secondary electronic device. Further, in additional embodiments, the device may include a sensor adapted to detect the current position of the wearer and activate the vibration mechanism accordingly. In this way, the posture correction device is configured to instruct the wearer to move to a correct posture position or to adapt a more correct breath pattern.

In some embodiments, the device is operable for establishing deep, relaxed belly breathing, posture correction, concentration, mindfulness, meditative techniques and electro-magnetic massage. The device includes a housing having an adjustable strap that secures the housing to either the torso or waist of a wearer. In one embodiment, the housing further comprises an adhesive tab that secures the housing to the wearer. In additional embodiments, the base includes an internal vibration mechanism configured to vibrate or emit weak electrical pulses in a pre-determined time sequence in order to promote the health and well-being of the wearer. The device further includes controls to adjust the timing and intensity of the electrical pulses or vibrations. The housing may comprise a switch that is slidably moveable along a complementary track, wherein a wearer may modulate the intensity of the electrical pulses or vibrations of the internal vibration mechanism. Further, the housing may comprise a rhomboidal cross-section, wherein four beveled brackets extend downwardly from an upper surface of each end of the housing. In one embodiment, each bracket includes the internal vibration mechanism, such that a substantial portion of the wearer's body receives the pulse or vibration when the internal vibration mechanism is activated.

In further embodiments, in one configuration, a pair of adjustable straps extends outwardly from each end of the housing, whereby the pair of adjustable straps is arranged in an X-shaped configuration. In this way, each adjustable strap secures diagonally across the torso of the wearer, wherein the housing contacts a portion of the wearer's back. In another configuration, one adjustable strap extends about the waist of the wearer, such that the housing contacts a desired portion along the wearer's waist, such as their side.

In some embodiments, the device may include a wireless transceiver that is operable for enabling the internal vibration mechanism to be wirelessly controlled via a smartphone or other secondary electronic device that is programmed to control the device. Further, in some embodiments, the device includes a sensor adapted to detect the current position or breathe pattern of the wearer and activate the vibration mechanism accordingly instruct the wearer to move to a correct posture position or to adapt a more correct breathing pattern.

In further embodiments, the device may comprise a means for achieving a state of Zen or a state of awareness. The device may enhance attentiveness and concentration, to aid in the digestion of topics and materials. And in many other situations, where real presence is necessary. The device may repeatedly increase a wearer presence at a consciousness level and after some time, the wearer may always be calm and attentive. The device may aid a wearer to achieve a state the Zen or awareness, and also to become a great listener, in hearing of lectures, at lessons, when reading books and documentation. When hearing audiobooks and other materials and also in many other situations where awareness is required.

The present invention will now be described in detail with reference to embodiments thereof as illustrated in the accompanying drawings.

FIG. 1 shows in (1A), (1B), and (1C), an exemplary perspective view of a posture correction device while disposed on a torso of a wearer, in accordance with an embodiment of the present invention. FIG. 1A shows a back view of wearer 115. FIG. 1B shows a front view of wearer 115. FIG. 1C shows a perspective view of wearer 115. Posture correction device 100 may comprise a housing that may be secured on the torso of the wearer with pair of adjustable straps/harness 100. The pair of adjustable straps extends outwardly from each end of the housing through left strap attachment portion 390 (FIG. 3) and right strap attachment portion 520 (FIG. 5), whereby the pair of adjustable straps is arranged in an X-shaped configuration. In this way, each adjustable strap secures diagonally across the torso of the wearer, wherein the housing contacts a portion of the wearer's back. Posture correction device 100 may vibrate upon sensing an incorrect posture of the wearer, incorrect breath pattern, or upon sending an awareness signal to the device via a control device. The control device may comprise of, but not limited to, a smartphone, a remote controller, or similar control devices.

Figure 2:
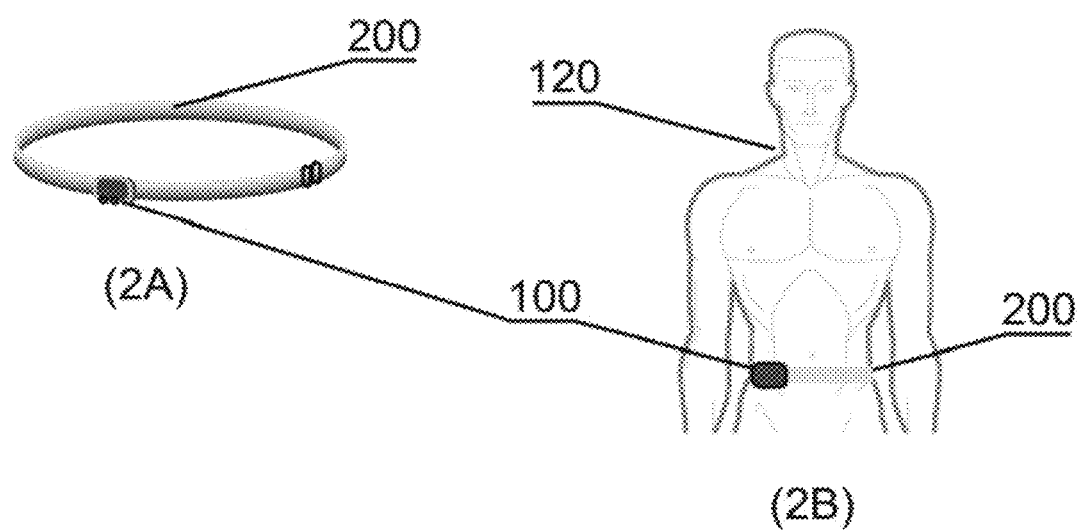
FIG. 2 shows an additional perspective view of an embodiment of the posture correction device while disposed on a wearer, in accordance with an embodiment of the present invention.
Figure 3:
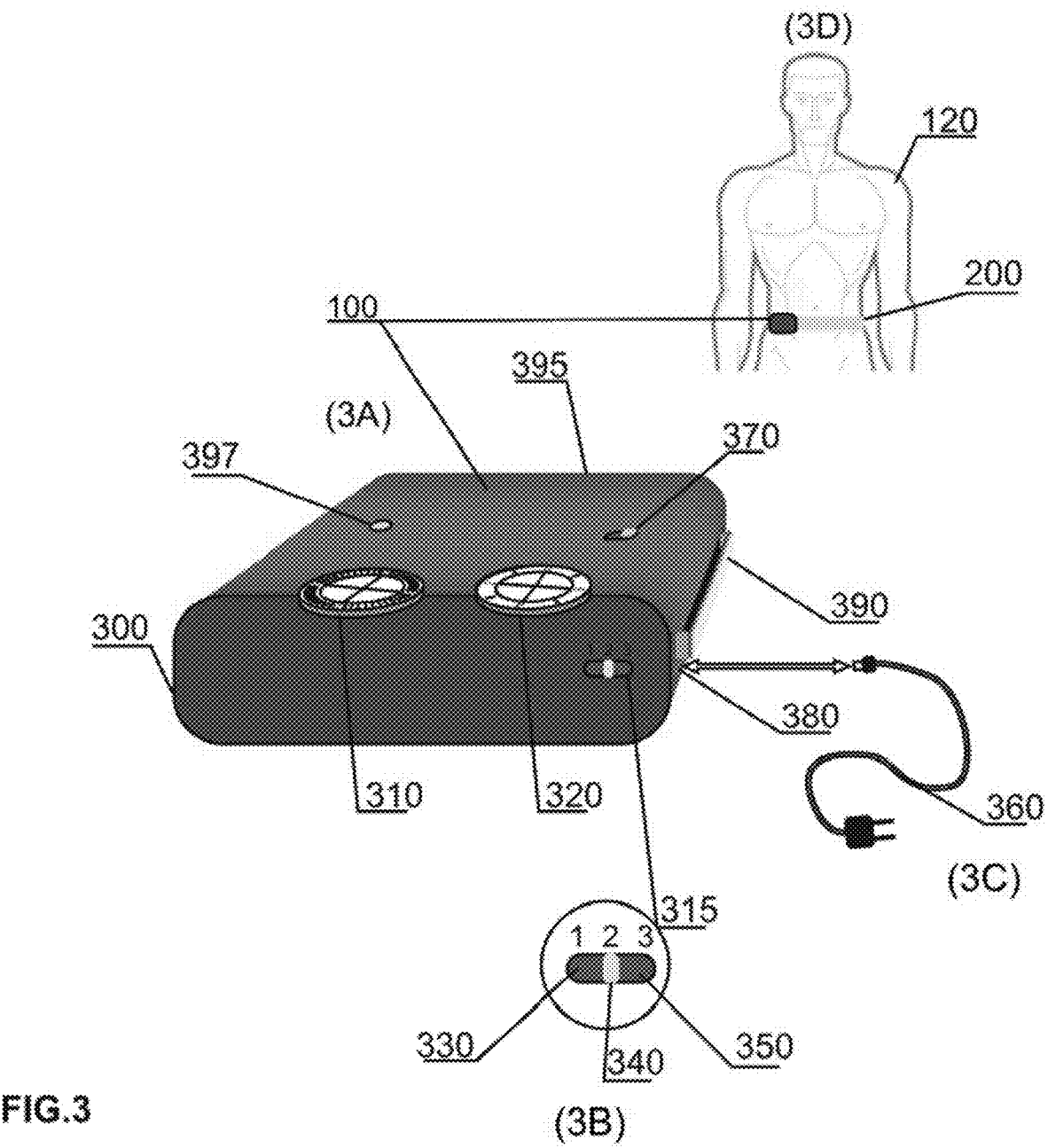
FIG. 3 is an illustration of an exemplary posture correction device, in accordance with an embodiment of the present invention.
Figure 5:
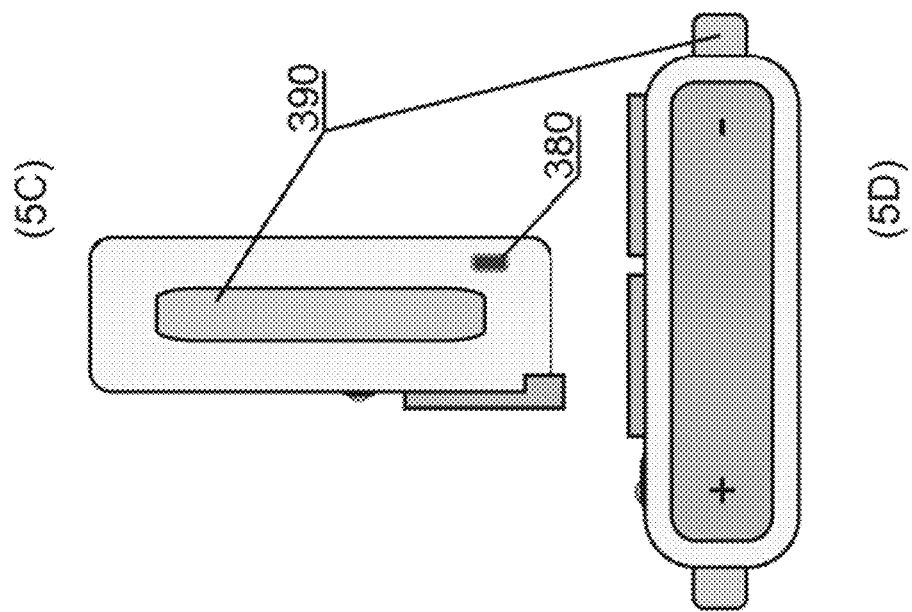
FIG. 5 is an illustration of an exemplary posture correction device while disposed on a wearer and in use, in accordance with an embodiment of the present invention.
Figure 5:
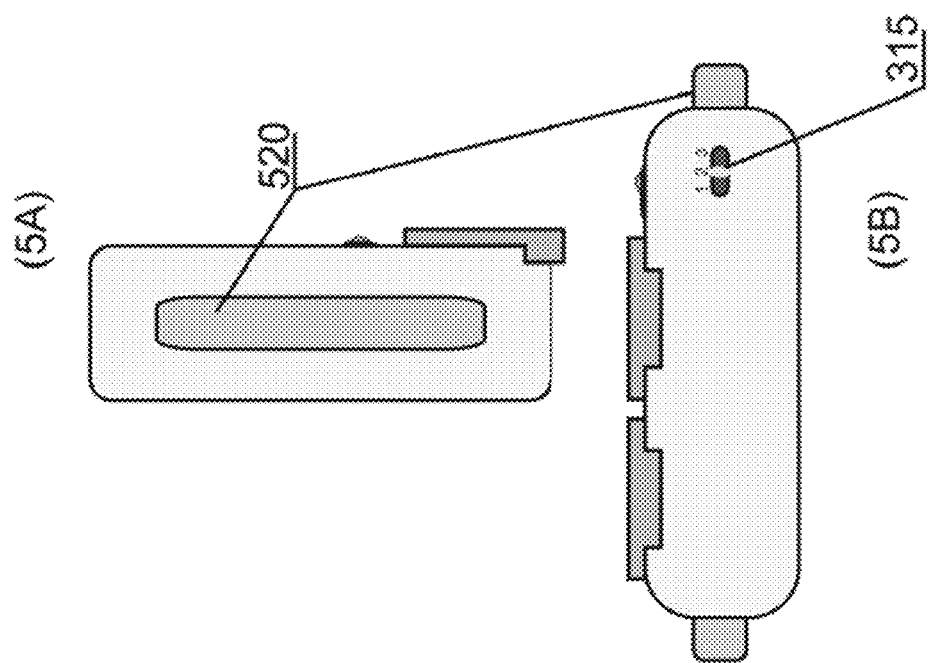

FIG. 2 shows in (2A) and (2B) an additional exemplary perspective view of the posture correction device while disposed on a waist of wearer 115, in accordance with an embodiment of the present invention. Posture correction device 100 may be secured to adjustable strap 200, as shown in FIG. 2A, with left strap attachment portion 390 (FIG. 3) and right strap attachment portion 520 (FIG. 5). Adjustable strap 200 is configured to extend about the waist of the wearer, such that the housing contacts a desired portion along the wearer's waist, including but not limited to a proximate side of the wearer, as shown in FIG. 2B. The adjustable strap extends outwardly from each end of the housing through securement portion 390 (FIG. 3). In this way, the adjustable strap secures across the waistline of the wearer, wherein the housing contacts a portion of the wearer's waist. Posture correction device 100 may vibrate upon sensing an incorrect posture of the wearer, incorrect breath pattern, or upon sending an awareness signal to the device via a control device. The control device may comprise of, but not limited to, a smartphone, a remote controller, or similar control devices.

FIG. 3 is an illustration of an exemplary posture correction device, in accordance with an embodiment of the present invention. Posture correction device 100, as shown in FIG. 3A, may include base 300 having an internal vibration mechanism configured to vibrate or emit weak electrical pulses in a pre-determined time sequence in order to signal the wearer to correct an incorrect posture or to correct an incorrect breath pattern, to promote the health and well-being of the wearer. The device further includes controls to adjust the timing and intensity of the electrical pulses or vibrations. In the illustrated embodiment, the device may comprise timing/timer dial 310 and vibration intensity/strength dial 320 for adjusting the timing and intensity/strength of the electrical pulses or vibrations. The device may further comprise switch 315 that is slidably moveable along a complementary track for indicating a function/activity to be monitored and controlled, such as but not limited to, shoulder/correct posture setting 330, deep breath/breath pattern setting 340, and Zen/awareness setting 350, wherein a wearer may modulate the intensity/strength of the electrical pulses or vibrations of the internal vibration mechanism based on the dial setting. Further, in the illustrated embodiment, the housing comprises a rhomboidal cross-section, wherein four beveled brackets extend downwardly from an upper surface of each end of the housing. In one embodiment, each bracket includes the internal vibration mechanism, such that a substantial portion of the wearer's body receives the pulse or vibration when the internal vibration mechanism is activated. In further embodiments, posture correction device 100 may further comprise USB charging cable 360 for connecting the device to an electrical outlet, lock 370, USD charging port 380 for charging device, right strap attachment portion 390, Zen logo 395, and charge/power indicator 397.

Figure 4:
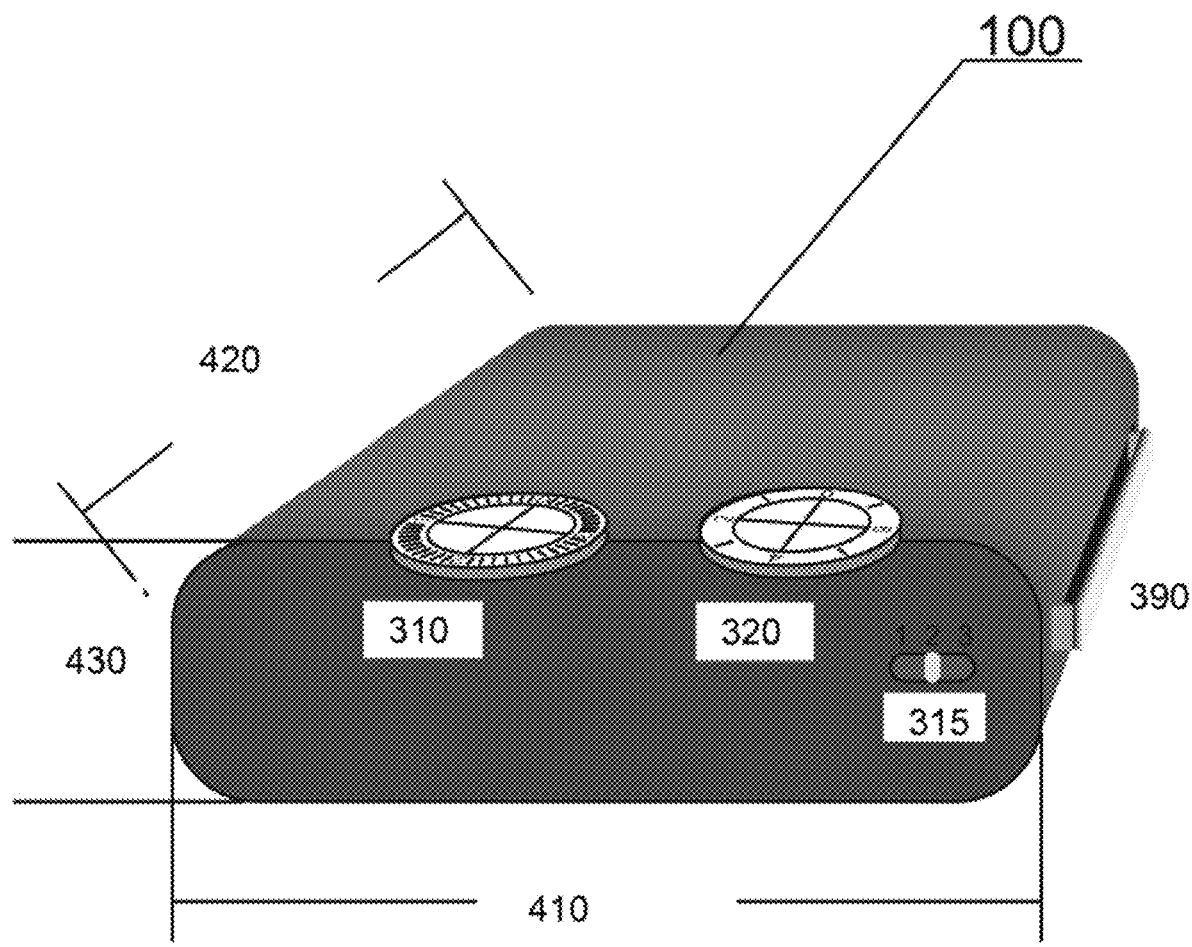
FIG. 4 shows a close-up view of an embodiment of the posture correction device, in accordance with an embodiment of the present invention.

FIG. 4 shows a close-up view of posture correction device 100, in accordance with an embodiment of the present invention. Posture correction device 100 housing may have a length 410 of about 50 to 60 mm, a width 420 of about 40-45 mm, and a height 430 of about 8-10 mm.

FIG. 5 is an illustration of exemplary posture correction device 100, in accordance with an embodiment of the present invention. FIG. 5A depicts a left side view of posture correction device 100 showing left strap attachment portion 390 and USD charging port 380. FIG. 5B depicts a front view showing slidable switch 315. FIG. 5C depicts a right side view showing right strap attachment portion 520. FIG. 5D depicts a back view showing battery component 510 and right strap attachment portion 520.

Figure 6:
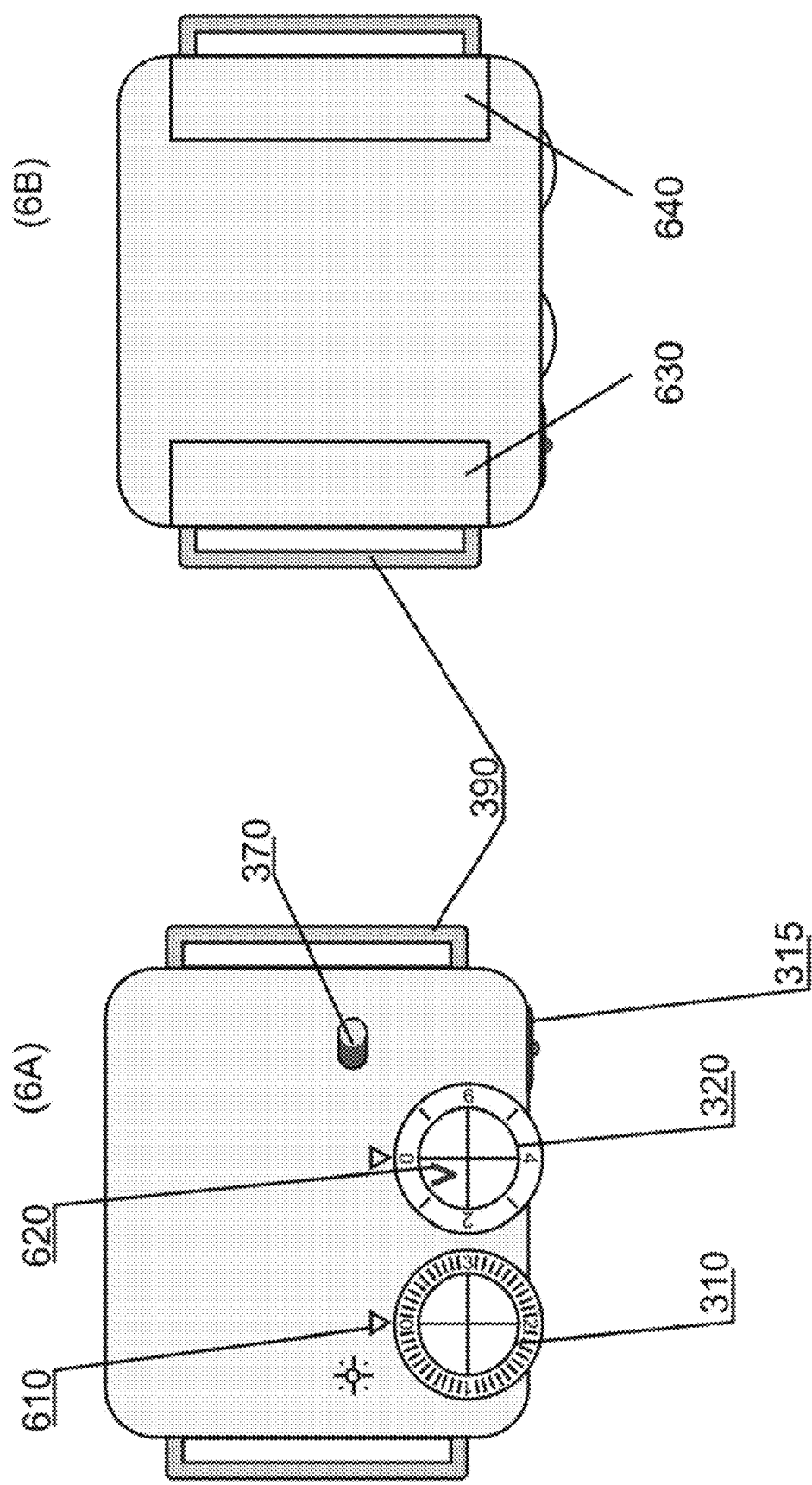
FIG. 6 is an illustration of an exemplary posture correction device, in accordance with an embodiment of the present invention.

FIG. 6 is an illustration of exemplary posture correction device 100, in accordance with an embodiment of the present invention. FIG. 6A depicts a top view of exemplary posture correction device 100 showing power indicator 610, vibration intensity/strength 620, lock 370, timing/timer dial 310 and vibration intensity/strength dial 320. FIG. 6B depicts a bottom view showing first steel contact 630, second steel contact 640, left strap attachment portion 390, and right strap attachment portion 520.

Figure 7:
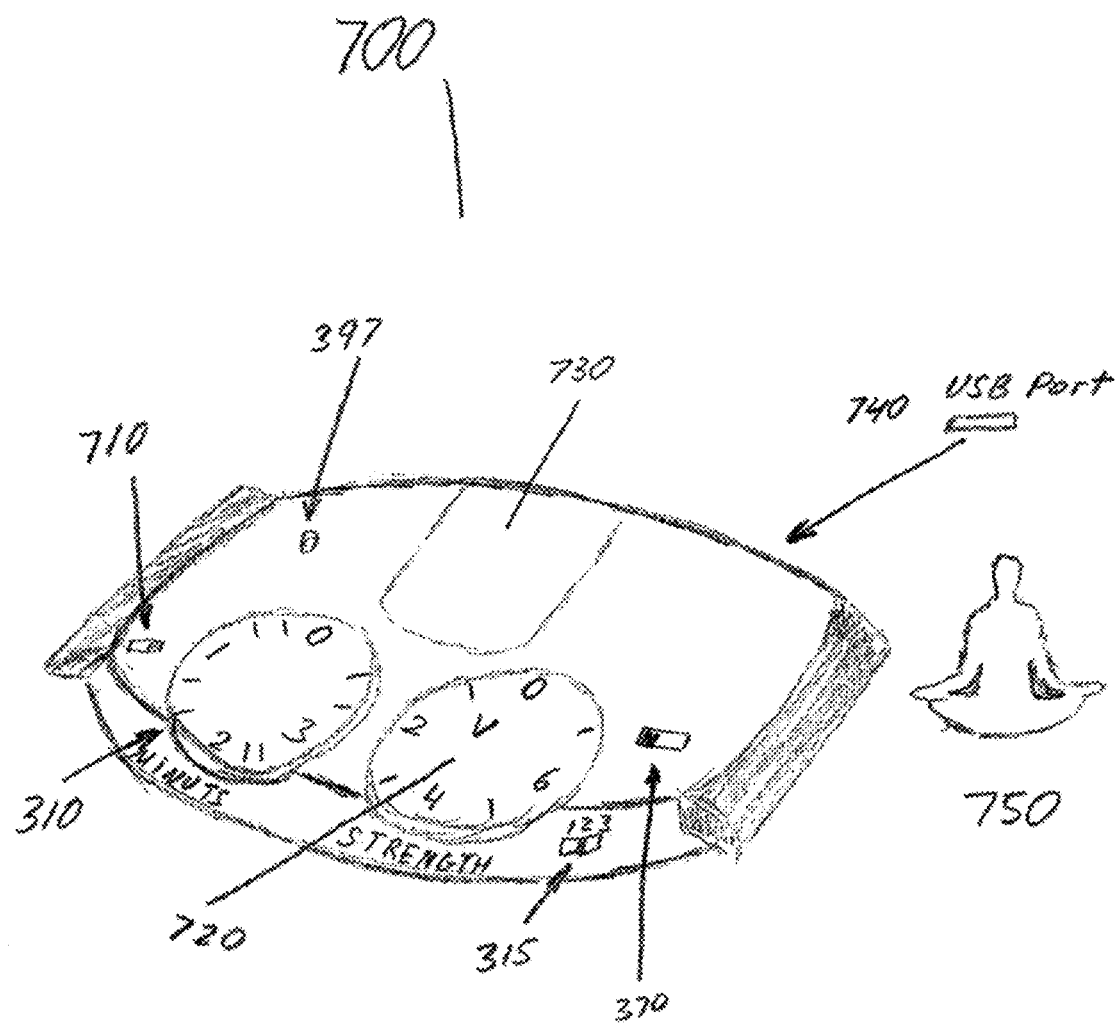
FIG. 7 is an illustration of an alternative exemplary posture correction device, in accordance with an embodiment of the present invention.

FIG. 7 is an illustration of an alternative exemplary posture correction device, in accordance with an embodiment of the present invention. Alternative posture correction device 700 incorporate posture correction device 100 with additional sensor switch 710, position controller 720 for indicating a first position V (vibration) before going to impulses, logo display area 730, USB charging port 740, where the port was moved from the side of the device to the back, and Zen logo 750.

Those skilled in the art will readily recognize, in light of and in accordance with the teachings of the present invention, that any of the foregoing steps and/or system modules may be suitably replaced, reordered, removed and additional steps and/or system modules may be inserted depending upon the needs of the particular application, and that the systems of the foregoing embodiments may be implemented using any of a wide variety of suitable processes and system modules, and is not limited to any particular computer hardware, software, middleware, firmware, microcode and the like. For any method steps described in the present application that can be carried out on a computing machine, a typical computer system can, when appropriately configured or designed, serve as a computer system in which those aspects of the invention may be embodied. Such computers referenced and/or described in this disclosure may be any kind of computer, either general purpose, or some specific purpose computer such as, but not limited to, a workstation, a mainframe, GPU, ASIC, etc. The programs may be written in C, or Java, Brew or any other suitable programming language. The programs may be resident on a storage medium, e.g., magnetic or optical, e.g., without limitation, the computer hard drive, a removable disk or media such as, without limitation, a memory stick or SD media, or other removable medium. The programs may also be run over a network, for example, with a server or other machine sending signals to the local machine, which allows the local machine to carry out the operations described herein.

Those skilled in the art will readily recognize, in light of and in accordance with the teachings of the present invention, that any of the foregoing steps may be suitably replaced, reordered, removed and additional steps may be inserted depending upon the needs of the particular application. Moreover, the prescribed method steps of the foregoing embodiments may be implemented using any physical and/or hardware system that those skilled in the art will readily know is suitable in light of the foregoing teachings. For any method steps described in the present application that can be carried out on a computing machine, a typical computer system can, when appropriately configured or designed, serve as a computer system in which those aspects of the invention may be embodied. Thus, the present invention is not limited to any particular tangible means of implementation.

Figure 8:
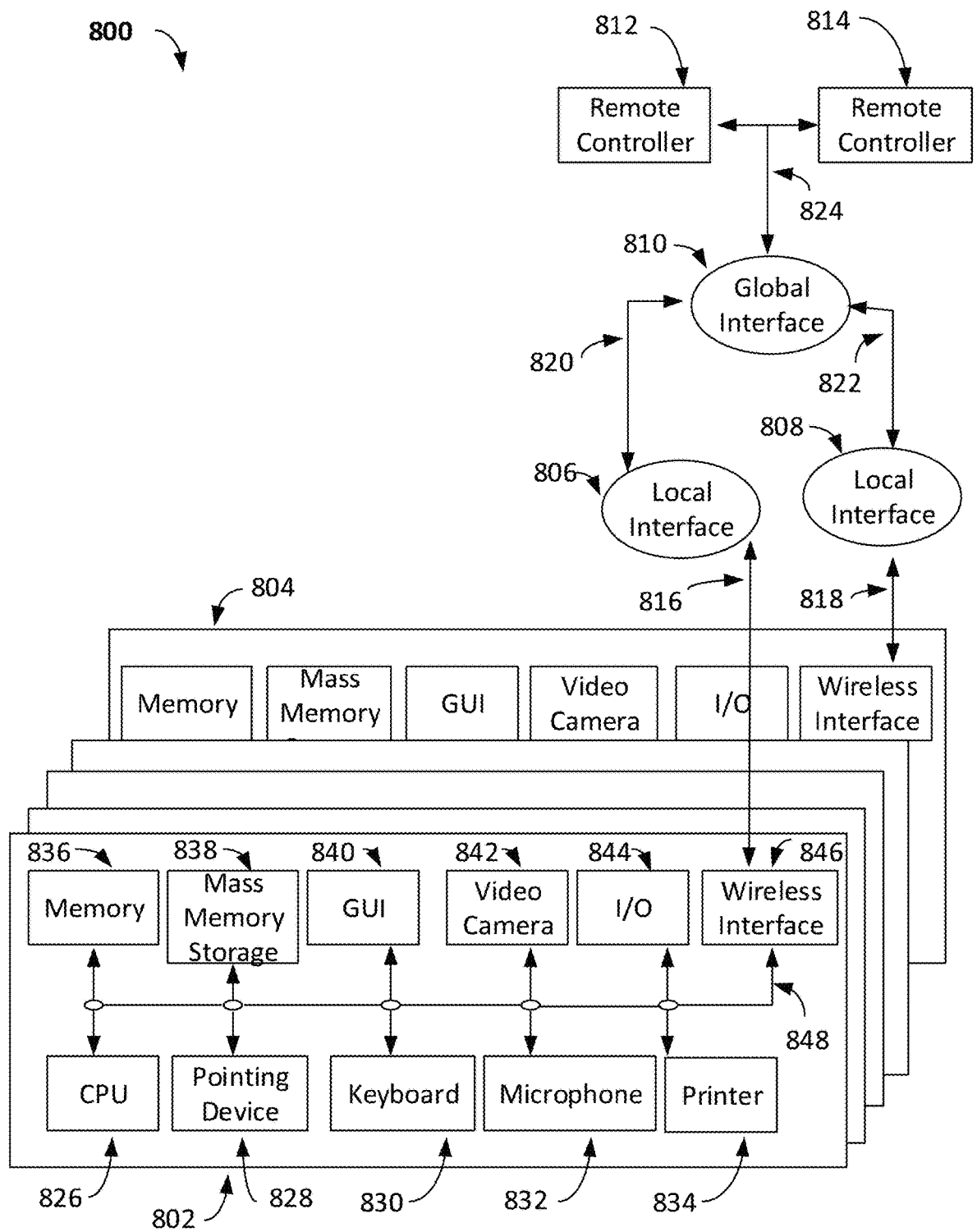
FIG. 8 illustrates a typical computer system that, when appropriately configured or designed, can serve as a computer system in which the posture correction device may be embodied, in accordance with an embodiment of the present invention.

FIG. 8 illustrates a typical computer system that, when appropriately configured or designed, can serve as a computer system 800 in which the posture correction device may be embodied. Computer system 800 includes a quantity of processors 802 (also referred to as central processing units, or CPUs) that are coupled to storage devices including a primary storage 806 (typically a random access memory, or RAM), a primary storage 804 (typically a read only memory, or ROM). CPU 802 may be of various types including micro-controllers (e.g., with embedded RAM/ROM) and microprocessors such as programmable devices (e.g., RISC or SISC based, or CPLDs and FPGAs) and devices not capable of being programmed such as gate array ASICs (Application Specific Integrated Circuits) or general purpose microprocessors. As is well known in the art, primary storage 804 acts to transfer data and instructions uni-directionally to the CPU and primary storage 806 is used typically to transfer data and instructions in a bi-directional manner. The primary storage devices discussed previously may include any suitable computer-readable media such as those described above. A mass storage device 808 may also be coupled bi-directionally to CPU 802 and provides additional data storage capacity and may include any of the computer-readable media described above. Mass storage device 808 may be used to store programs, data and the like and is typically a secondary storage medium such as a hard disk. It will be appreciated that the information retained within the mass storage device 808, may, in appropriate cases, be incorporated in standard fashion as part of primary storage 806 as virtual memory. A specific mass storage device such as a CD-ROM 814 may also pass data uni-directionally to the CPU.

CPU 802 may communicate with a remote controller 812. Alternatively, CPU 802 may be coupled to an interface 810 that connects to one or more remote control devices such as but not limited a smartphone, computer, or electronic control device using an external connection shown generally as a remote controller 812, which may be implemented as a hardwired or wireless communications link using suitable conventional technologies. With such a connection, the CPU might receive commands from the remote controller in the course of performing the method for establishing deep, relaxed belly breathing, posture correction, concentration, mindfulness, meditative techniques and electro-magnetic massage described in the teachings of the present invention.

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

It is noted that according to USA law 35 USC § 112(1), all claims must be supported by sufficient disclosure in the present patent specification, and any material known to those skilled in the art need not be explicitly disclosed. However, 35 USC § 112 (6) requires that structures corresponding to functional limitations interpreted under 35 USC § 112 (6) must be explicitly disclosed in the patent specification. Moreover, the USPTO's Examination policy of initially treating and searching prior art under the broadest interpretation of a "mean for" or "steps for" claim limitation implies that the broadest initial search on 35 USC § 112(6) (post AIA 112(f)) functional limitation would have to be conducted to support a legally valid Examination on that USPTO policy for broadest interpretation of "mean for" claims. Accordingly, the USPTO will have discovered a multiplicity of prior art documents including disclosure of specific structures and elements which are suitable to act as corresponding structures to satisfy all functional limitations in the below claims that are interpreted under 35 USC § 112(6) (post AIA 112(f)) when such corresponding structures are not explicitly disclosed in the foregoing patent specification. Therefore, for any invention element(s)/structure(s) corresponding to functional claim limitation(s), in the below claims interpreted under 35 USC § 112(6) (post AIA 112(f)), which is/are not explicitly disclosed in the foregoing patent specification, yet do exist in the patent and/or non-patent documents found during the course of USPTO searching, Applicant(s) incorporate all such functionally corresponding structures and related enabling material herein by reference for the purpose of providing explicit structures that implement the functional means claimed. Applicant(s) request(s) that fact finders during any claims construction proceedings and/or examination of patent allowability properly identify and incorporate only the portions of each of these documents discovered during the broadest interpretation search of 35 USC § 112(6) (post AIA 112(f)) limitation, which exist in at least one of the patent and/or non-patent documents found during the course of normal USPTO searching and or supplied to the USPTO during prosecution. Applicant(s) also incorporate by reference the bibliographic citation information to identify all such documents comprising functionally corresponding structures and related enabling material as listed in any PTO Form-892 or likewise any information disclosure statements (IDS) entered into the present patent application by the USPTO or Applicant(s) or any 3$^{rd}$ parties. Applicant(s) also reserve its right to later amend the present application to explicitly include citations to such documents and/or explicitly include the functionally corresponding structures which were incorporate by reference above.

Thus, for any invention element(s)/structure(s) corresponding to functional claim limitation(s), in the below claims, that are interpreted under 35 USC § 112(6) (post AIA 112(f)), which is/are not explicitly disclosed in the foregoing patent specification, Applicant(s) have explicitly prescribed which documents and material to include the otherwise missing disclosure, and have prescribed exactly which portions of such patent and/or non-patent documents should be incorporated by such reference for the purpose of satisfying the disclosure requirements of 35 USC § 112(6). Applicant(s) note that all the identified documents above which are incorporated by reference to satisfy 35 USC § 112(6) necessarily have a filing and/or publication date prior to that of the instant application, and thus are valid prior documents to incorporated by reference in the instant application.

Having fully described at least one embodiment of the present invention, other equivalent or alternative methods of implementing posture correction devices according to the present invention will be apparent to those skilled in the art. Various aspects of the invention have been described above by way of illustration, and the specific embodiments disclosed are not intended to limit the invention to the particular forms disclosed. The particular implementation of the posture correction device may vary depending upon the particular context or application. By way of example, and not limitation, the posture correction device described in the foregoing were principally directed to establishing deep, relaxed belly breathing, posture correction, concentration, mindfulness, meditative techniques and electro-magnetic massage implementations; however, similar techniques may instead be applied to patient rehabilitation, which implementations of the present invention are contemplated as within the scope of the present invention. The invention is thus to cover all modifications, equivalents, and alternatives falling within the spirit and scope of the following claims. It is to be further understood that not all of the disclosed embodiments in the foregoing specification will necessarily satisfy or achieve each of the objects, advantages, or improvements described in the foregoing specification.

Claim elements and steps herein may have been numbered and/or lettered solely as an aid in readability and understanding. Any such numbering and lettering in itself is not intended to and should not be taken to indicate the ordering of elements and/or steps in the claims.

The corresponding structures, materials, acts, and equivalents of all means or step plus function elements in the claims below are intended to include any structure, material, or act for performing the function in combination with other claimed elements as specifically claimed.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The Abstract is provided to comply with 37 C.F.R. Section 1.72(b) requiring an abstract that will allow the reader to ascertain the nature and gist of the technical disclosure. That is, the Abstract is provided merely to introduce certain concepts and not to identify any key or essential features of the claimed subject matter. It is submitted with the understanding that it will not be used to limit or interpret the scope or meaning of the claims.

The following claims are hereby incorporated into the detailed description, with each claim standing on its own as a separate embodiment.

Only those claims which employ the words "means for" or "steps for" are to be interpreted under 35 USC 112, sixth paragraph (pre AIA) or 35 USC 112(f) post-AIA. Otherwise, no limitations from the specification are to be read into any claims, unless those limitations are expressly included in the claims.

What is claimed is:

1. A device comprising:
   a vibration mechanism, said vibration mechanism is configured to at least one of vibrate and emit electrical pulses in a pre-determined time sequence, wherein said vibration mechanism is configured to signal a wearer to at least one of correct an incorrect posture, correct an incorrect breathing pattern of the wearer to promote a health and well-being of the wearer, and keep the consciousness of the wearer active or attentive;

a deep breath pattern function setting element, wherein said deep breath pattern function setting element is configured to be operable for signaling the wearer to rectify a detected incorrect breathing pattern, a Zen or awareness function setting element, wherein said Zen or awareness function setting element is configured to be operable for sending an awareness signal to enhance attentiveness and concentration of the wearer;

a switch unit, said switch unit is configured to slidably move along a track portion for indicating the function setting to be monitored or controlled; and means for providing power to said device.

2. A device comprising:

a vibration mechanism, said vibration mechanism is configured to at least one of vibrate and emit electrical pulses in a pre-determined time sequence, wherein said vibration mechanism is configured to signal a wearer to at least one of correct an incorrect posture, correct an incorrect breathing pattern of the wearer to promote a health and well-being of the wearer, and keep the consciousness of the wearer active or attentive;

a housing apparatus, said housing apparatus is configured to accommodate said vibration mechanism;

a timer dial implement, said timer dial implement is configured to be operable for adjusting a timing of said vibration mechanism;

an intensity or strength dial implement, said intensity or strength dial implement is configured to be operable for adjusting an intensity or strength of said at least one of vibration and electrical pulses;

a shoulder or correct posture function setting element, wherein said shoulder or correct posture function setting element is configured to be operable for signaling the wearer to correct a detected improper posture;

a deep breath pattern function setting element, wherein said deep breath pattern function setting element is configured to be operable for signaling the wearer to rectify a detected incorrect breathing pattern;

a Zen or awareness function setting element, wherein said Zen or awareness function setting element is configured to be operable for sending an awareness signal to enhance attentiveness and concentration of the wearer;

a switch unit, said switch unit is configured to slidably move along a track portion for indicating the function setting to be monitored or controlled; and an attachment portion, wherein said attachment portion is configured to secure said vibration mechanism to the wearer.

3. The device of claim 2, further comprising a control device including at least one of a smartphone and a remote controller.

4. The device of claim 3, further comprising a charging port that is configured to charge said device.

5. The device of claim 4, further comprising a charge or power indicator.

6. The device of claim 5, further comprising a battery holder.

7. The device of claim 6, further comprising a lock.

8. The device of claim 6, in which said housing apparatus comprises:

a left strap attachment component that is configured to engage said attachment portion on a left side section of said housing apparatus; and a right strap attachment component that is configured to engage said attachment portion to a right side section of said housing apparatus.

9. The device of claim 8, in which said attachment portion comprises a pair of adjustable straps, each adjustable strap comprises a first and second end constituent, wherein said first end constituent is configured to be engaged with said left strap attachment portion, and said second end constituent is configured to be engaged with said right strap attachment portion.

10. The device of claim 9, said pair of adjustable straps is operable to be arranged in an X-shaped configuration, and wherein each adjustable strap secures diagonally across a torso of the wearer, and wherein said housing apparatus contacts a portion of the wearer's back.

11. The device of claim 9, in which said attachment portion is configured to secure said housing apparatus to a waist of the wearer, said attachment portion comprises an adjustable strap including a first and second end constituent, wherein said first end constituent is configured to be engaged with said left strap attachment portion, and said second end constituent is configured to be engaged with said right strap attachment portion.

12. The device of claim 9, in which said housing apparatus further comprises a first steel contact implement.

13. The device of claim 12, in which said housing apparatus further comprises a first steel contact implement.

14. A device comprising:

a vibration mechanism, said vibration mechanism is configured to at least one of vibrate and emit electrical pulses in a pre-determined time sequence, wherein said vibration mechanism is operable for signaling a wearer to at least one of be aware of an incorrect posture, be aware of an incorrect breath pattern to promote a health and well-being of the wearer, and provide electromagnetic impulse massage;

a housing, said housing is configured to hold said vibration mechanism;

a battery holder for holding at least one or more batteries;

a charging port that is configured to charge said at least one or more batteries;

a charge or power indicator that is configured to visually provide an indication that said power is on or off;

a timer dial implement, said timer dial implement is configured to be operable for adjusting a timing pattern of said vibration mechanism;

an intensity or strength dial implement, said intensity or strength dial implement is configured to be operable for adjusting an intensity or strength of said at least one of vibration and electrical pulses;

a shoulder or correct posture function setting element, wherein said shoulder or correct posture function setting element is configured to be operable for alerting the wearer to correct a detected improper posture;

a deep breath pattern function setting element, wherein said deep breath pattern function setting element is configured to be operable for signaling the wearer to rectify a detected incorrect breathing pattern;

a Zen or awareness function setting element, wherein said Zen or awareness function setting element is configured to be operable for sending an awareness signal to enhance attentiveness and concentration of the wearer;

a switch unit, said switch unit is configured to slidably move along a track portion for indicating the function setting to be monitored or controlled; and an attachment portion, wherein said attachment portion is configured to secure said vibration mechanism to the wearer.

15. The device of claim 14, further comprising a lock.

16. The device of claim 15, in which said housing apparatus comprises:
   a left strap attachment component that is configured to engage said attachment portion on a left side section of said housing apparatus; and
   a right strap attachment component that is configured to engage said attachment portion to a right side section of said housing apparatus.

17. The device of claim 16, in which said attachment portion comprises a pair of adjustable straps, each adjustable strap comprises a first and second end constituent, wherein said first end constituent is configured to be engaged with said left strap attachment portion, and said second end constituent is configured to be engaged with said right strap attachment portion.

18. The device of claim 17, said pair of adjustable straps is operable to be arranged in an X-shaped configuration, and wherein each adjustable strap secures diagonally across a torso of the wearer, and wherein said housing apparatus contacts a portion of the wearer's back.

19. The device of claim 17, in which said attachment portion is configured to secure said housing apparatus to a waist of the wearer, said attachment portion comprises an adjustable strap including a first and second end constituent, wherein said first end constituent is configured to be engaged with said left strap attachment portion, and said second end constituent is configured to be engaged with said right strap attachment portion.

20. The device of claim 19, in which said housing apparatus further comprises a first steel contact implement and a second steel contact implement, said first and second contact implements being disposed at a base of said device.

* * * * *